United States Patent [19]

Lo

[11] 4,095,552
[45] Jun. 20, 1978

[54] DUMMY BEARING FOR BEARING WEAR DETECTION

[76] Inventor: Hewitt Hsu Fu Lo, 6100 Massachusetts Ave., Washington, D.C. 20016

[21] Appl. No.: 800,494

[22] Filed: May 25, 1977

[51] Int. Cl.² .................... F16C 41/00; G01N 3/56
[52] U.S. Cl. ............................. 116/114 Q; 73/7; 308/1 A
[58] Field of Search ............ 116/114 Q; 308/63, 1 A; 340/269; 73/7

[56] References Cited

U.S. PATENT DOCUMENTS

| | | | |
|---|---|---|---|
| 1,361,000 | 12/1920 | Blain | 116/114 Q |
| 2,750,240 | 6/1956 | Naab | 116/114 Q |
| 3,797,451 | 3/1974 | Tiraspolsky | 116/114 Q |
| 3,853,087 | 12/1974 | Aldag | 116/114 Q |

Primary Examiner—Daniel M. Yasich
Attorney, Agent, or Firm—R. Sciascia; R. Beers; S. Sheinbein

[57] ABSTRACT

Apparatus for detecting wear on radial or thrust bearings. Bearing clearances are monitored by observing clearances generated by dummy bearings structured to wear like the actual bearings and installed in proximity thereto and designed so that their clearances may be readily determined by direct inspection.

10 Claims, 6 Drawing Figures

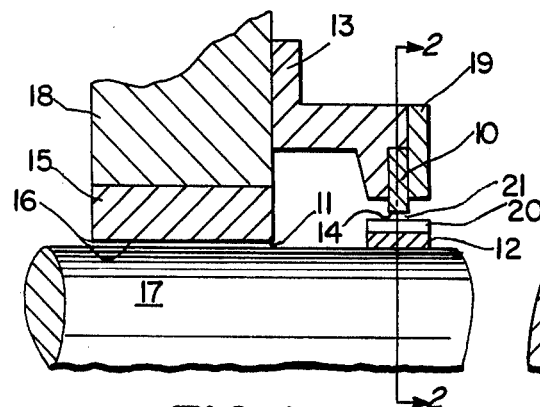
FIG. 1
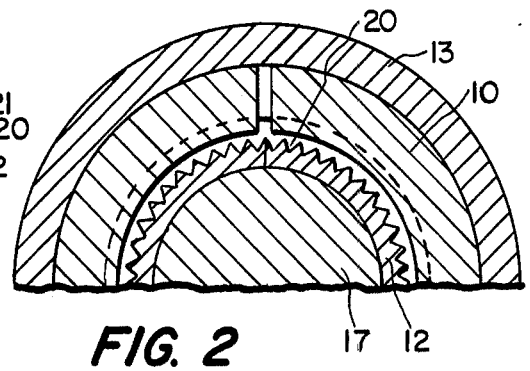
FIG. 2
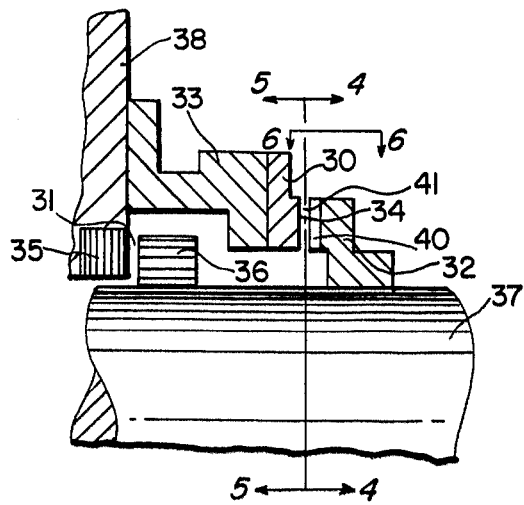
FIG. 3
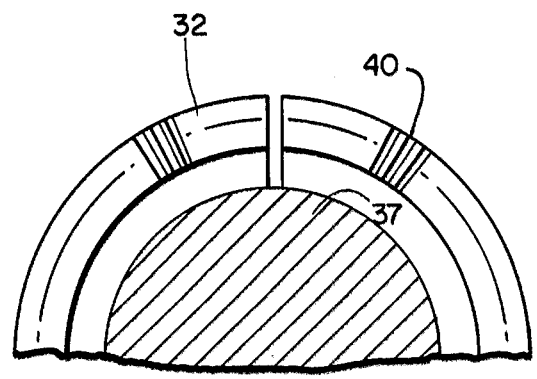
FIG. 4
FIG. 5
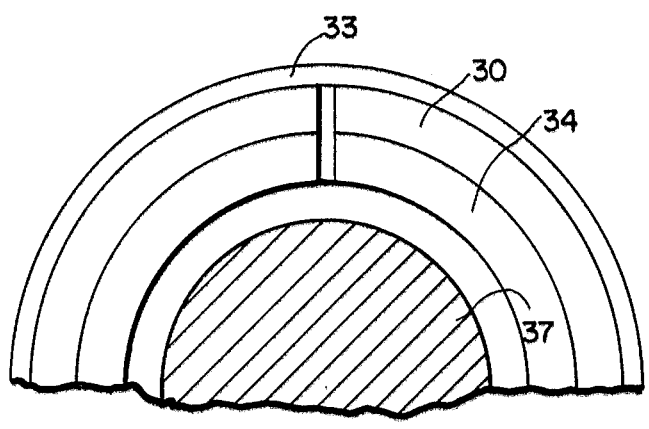
FIG. 6
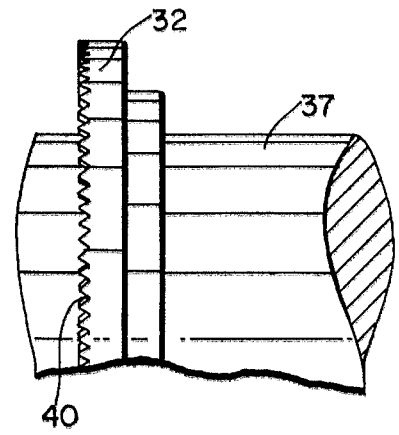

DUMMY BEARING FOR BEARING WEAR DETECTION

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to bearing control and more specifically to bearing wear detection.

In many applications, bearing failure can lead to costly damage to the machines in which the bearings are operating and provides a potential for breakdown at unknown and often inconvenient intervals. Therefore, devices for monitoring bearing wear have shown themselves to be indispensable. Bearings for moving machinery parts and shafts are usually securely covered and sealed for reasons of safety, to prevent foreign material from contaminating the bearing surfaces, and to contain lubricating fluids used in operation of the bearings. In general, shaft bearings are protected by oil or watertight seals and in some cases these seals cannot be removed while the shafts are still in operation or the seals are under high pressure fluid. Under such conditions, if the bearing clearances have to be measured to assure the operation of the machinery, the operation of the shaft has to be shut down, and the high fluid pressure behind the seals, if any, has to be brought down to a workable level before the bearing clearance measurements can be performed. It is known that bearing clearances of submarine control surfaces are measured by means of hydraulic jacks, lift from cranes, and dial gauges. However there were cases, utilizing the prior art measuring procedures, in which the bearings were opened up unnecessarily for repair since the bearings were subsequently found to be in good condition. To obviate the need for such time consuming and involved procedures various systems have been devised to remotely ascertain bearing clearances.

Prior art apparatus used to remotely monitor bearing wear operate in accordance with the principle of galvanic currents passing through the shaft and bearing whereby the illumination of a small lamp on metallic contact taking place between bearing and shaft serves as an indication of the critical condition. Variations on this system include the use of sets of wires annularly disposed around the bearing shaft so that any eccentricities in the rotation of the shaft induced by bearing wear lead to electrical contact which in turn triggers an alarm indicative of excessive bearing wear. However, in all of these systems, the input of electric current to the shaft requries contact points with the latter, e.g. brushes made of speical copper-graphite in contact with a needle mounted centrally on the shaft. This device has shown itself to be inadequate in view of the unavoidable material wear and in the inconsistancy of contact resistances.

An attempt has also been made to determine the magnitude of change in the lubrication gap between shaft and bearing with capacitive measuring devices. This system can only be used in special cases as a contact indicator, namely only in the case where the measuring device is situated at the same height as the load surface of the bearing and the if shaft touches the bearing at this point. Further, arrangements have been proposed whereby capacitive measurements or the clearance of a rotating body take place with the aid of fixed electrodes. With this arrangement, two electrodes are screened off from one another and an alternating voltage of constant amplitude and frequency is fed to one of the electrodes and the voltage arising at the second electrode due to capacitive coupling regulated by the rotating body is amplified and led to an indicating instrument. This system generally works well except that it does not allow the position or degree of the bearing wear to be remotely determined, it requires expensive equipment, and is subject to malfunction if impurities exist in the lubricating fluid.

SUMMARY OF THE INVENTION

Accordingly, the present invention provides for monitoring the wear on radial and thrust bearings by observation or measurement of clearances generated by a dummy bearing system. A ring is coaxially mounted on the shaft of the bearing to be monitored so that it rotates with the shaft. A second ring is secured to the bearing, independent of the shaft, so as to remain stationary, and is positioned outwardly surrounding to the first ring so that any irregularities in the pattern of rotation of the hsaft will lead to contact and wear between the two rings. Inasmuch as irregularities in the pattern of rotation are generally caused by bearing wear, wear on the rings is indicative of wear on the actual bearing, and by inspection or measurement of the rings, bearing wear may be determined and measured.

OBJECTS OF THE INVENTION

It is therefore an object of the present invention to provide for reliably and accurately determining bearing wear.

Another object of the present invention is to provide a bearing wear detector which is simple and inexpensive to construct.

Another object of the present invention is to provide a reliable method of bearing clearance measurements in propellor line shafts, reduction gear, turbine rotors and ship control surface stocks.

A further object of the present invention is to provide a bearing wear detector which can determine the location and amount of wear on a bearing.

A yet further object of the present invention is to provide a bearing wear detector which will allow bearing wear to be ascertained while the associated machinery is in operation thereby avoiding costly shutdowns.

A still further object of the present invention is to provide a bearing wear detector of rugged design which will allow bearing wear to be quickly and continuously monitored.

BRIEF DESCRIPTION OF THE DRAWINGS

These and other objects, features and attendant advantages of the present invention will be more readily apparent to those skilled in the art from a consideration of the following specification including the claim and drawings, wherein:

FIG. 1 is a central sectional view along the longitudinal axis of one embodiment of the device according to the invention installed on a radial bearing;

FIG. 2 is a vertical sectional view taken along the line 2—2 of FIG. 1;

FIG. 3 is a central sectional view along the longitudinal axis of a second embodiment of the device according to the invention installed on a thrust bearing;

FIG. 4 is a vertical sectional view taken along line 4—4 of FIG. 3;

FIG. 5 is a vertical sectional view taken approximately along line 5—5 of FIG. 3; and FIG. 6 is a side view along line 6—6 of FIG. 3.

DESCRIPTION OF THE PREFERRED EMBODIMENT

Referring now to the drawings wherein like reference characters designate like or corresponding parts throughout the several views, FIGS. 1 and 2 illustrate different sections of one embodiment of the invention installed on a radial bearing 15 and shaft 17 journalled within the bearing. For the sake of clarity, the bearing covers and seals are not shown. A split ring 10 of fixed and recorded width is clamped or pinned to the dummy bearing housing 13 so that its inner surface 14 is facing the shaft 17 and is held parallel to the inside surface 16 of bearing 15. Ring 10 is constructed of a noncorrosive soft material of good machinability so that it may be easily cut and lubricating oil may carry away any worn off bits without interfering with the operation of the apparatus. The dummy bearing housing 13 is in turn pinned to the bearing support structure 18 so that it and split ring 10 are held fixed and stationary relative to shaft 17. A cover plate 19 is secured to dummy bearing housing 13 to overlay the split ring 10 and shield it.

A second split ring 12 is keyed or clamped onto the shaft 17 in inward surrounding relation to split ring 10 so that a gap 21 equal to the clearance 11 between shaft 17 and bearing 15 is formed between split ring 10 and split ring 12. Ring 12 has a series of saw-tooth like cutting edges 20 on its exterior surface and is constructed of a material much harder than the material of ring 10 so that the wear on split ring 12 will be negligible. Further, as with split ring 10, ring 12 should be of a noncorrosive material. The cutting edges 20 are equidistant from the centerline of shaft 17 so that the cutting edges 20 and the surface 14 of ring 10 simulate the relationship of the shaft 17 to the surface of the bearing 15 and form the "dummy bearing" of the present invention.

In operation, wear on the bearing surface 15 causes eccentric or irregular patterns of rotation for shaft 17. Eccentricities or irregularities in the pattern of rotation of the shaft 17 in turn lead cutting edges 20 to abrade the surface 14 of the soft material of ring 10 in a pattern circumferentially proportional to the pattern of wear on bearing 15.

Therefore, to measure the wear or clearance of the bearing 15 it is but necessary to measure the radial width of the dummy bearing. Furthermore, the bearing clearances can be expressed by the following equation:

$$(BC)_i = (D)_i - (E)_i + (F)_i \qquad (1)$$

$(BC)$—bearing clearance 11
$(D)$—width of radial dummy bearing 10, initial
$(E)$—measured width of the radial dummy bearing which has been worn
$(F)$—initial bearing clearance 21
$i$—subscript indicating the corresponding dummy bearing clearance position with respect to the circumference of the bearing. For example, $i$ may represent 0°, 5°, etc.

Equation (1) is accurate so long as the dummy bearing is installed close to the bearing 15 and shaft deflections are small. When a dummy bearing is installed far from a bearing, corrections should be applied to equation (1) to take into account of the shaft deflections.

FIGS. 3, 4, 5 and 6 show various sections and views of a second embodiment of the invention installed on a thrust bearing 35 and shaft 37 journalled within that bearing. For the sake of clarity, the bearing covers and seals are not shown. A split ring 30 of fixed and recorded thickness is pinned to dummy bearing housing 33 so that its outer surface 34 facing away from the bearing 35 is held parallel to the working surface 36 of the bearing. Ring 30 is constructed of a soft material of good machinability so that it may be easily cut and lubricating oil may carry away worn off bits without interfering with the operation of the apparatus. The dummy bearing housing 33 is pinned to the bearing support structure 38 so that the split ring 30 is held fixed and stationary relative to the shaft 37. A second split ring 32 is keyed or clamped onto the shaft 37 so that it is adjacent to and faces ring 30 along the longitudinal axis and that a gap 41, equal to the initial bearing clearance 31, is formed between split ring 30 and split ring 32. Ring 32 has a series of saw-tooth like cutting edges 40 on the surface facing ring 30 constructed of a material comparatively much harder than the material of ring 30. Initially, the cutting edges 40 are all equally distant from the surface of ring 30 so that the cutting edges 40 and the ring 30 simulate the relationship of the shaft 37 to the bearing 35 and form the "dummy bearing" of the present invention. Both ring 30 and 32 should be of a noncorrosive material so that the cutting edges will be retained if in a water environment.

In operation, wear on the bearing surface 36 causes the rotational axis of the shaft 37 to shift toward the bearing 35. This shift subsequently causes cutting edges 40 to abrade the surface 34 of ring 30 in a pattern circumferentially proportional to the pattern of wear on the bearing 35. Therefore, to measure the wear or clearance of the thrust bearing 35 one merely measures the longitudinal width of the dummy bearing. Furthermore, the bearing wear can be expressed by the following equation:

$$(BC)_i = (D)_i - (E)_i + (F)_i \qquad (2)$$

Where:
$(BC)_i$—bearing clearance
$(D)$—thickness of dummy bearing 30, initial
$(E)$—thickness of dummy bearing measured for thrust bearing clearance
$(F)$—initial thrust bearing clearance 41
$i$—subscript indicating the corresponding thrust dummy bearing clearance position with respect to the circumference of the thrust bearing. For example $i$ may represent 0°, 2°, etc.

Equation (2) is accurate so long as the dummy bearing is installed close to the bearing 35 and shaft deflections are small. When a dummy bearing is installed far from a account for shaft deflections.

As was noted the radial and thrust dummy bearings should be installed as close to the radial bearing and the thrust bearing as possible, respectively, to ensure more direct bearing clearances generated by the dummy bearing system. However, if a dummy bearing is located a considerable distance away from a bearing, the true bearing clearance can be found by appropriate corrections. These corrections are based on a geometric relationship of the shaft deflection and the measured bearing clearances generated by the split ring mounted on the shaft.

Thus it is apparent that the present invention provides a bearing wear detection system whereby actual bearing clearances can be accurately obtained by measuring clearances generated by a dummy bearing system. Further, bearing wear can often be measured while machinery is in operation, obviating unnecessary openings of good bearings and providing optimum performance until the known service life of the bearing is reached.

It is therefore to be understood that what has been described is merely illustrative of the principles of the invention and that numerous arrangements in accordance with this invention may be devised by one skilled in the art without departing from the spirit and scope thereof. For example, the radial type of dummy bearing could be constructed without the split ring mounted on the shaft if the hardness of shaft surface or the shaft sleeve under the dummy bearing is comparatively much harder than the radial dummy bearing. Other modifications may omit split ring 12 and have the cutting edges placed on the surface of the shaft 17, or the cutting edges could be placed on ring 10 in such a position that they would abrade ring 12. Many similar variations would be possible.

What is new and desired to be secured by Letters Patent of the United States is:

1. A dummy bearing for indicating the state of wear of a bearing journalling a shaft in a support comprising:
   a housing affixed to the bearing support;
   a readily observable annular member positionally secured to said housing and disposed about and proximate said shaft; said annular member being fixed relative to said shaft and proximate said bearing;
   abrading means on said shaft proximate said annular member,
   whereby upon excessive bearing wear, said shaft resultingly rotates in an irregular or eccentric pattern causing said abrading means to wear said annular member so that an indication of the wear of said bearing is provided by visual inspection and measurement of the amount of abrasion of the surface of said annular member.

2. The dummy bearing of claim 1, wherein said annular member is a first split ring.

3. The dummy bearing of claim 2, wherein said first split ring is composed of a non-corrosive, soft material which simulates the wearing characteristics of said bearing.

4. The dummy bearing of claim 2, wherein said first split ring is attached to a stationary dummy bearing housing which is located proximate said bearing in order to provide an accurate indication of the wear of said bearing.

5. The dummy bearing of claim 1, wherein said abrading means comprises a second split ring fixed on said shaft.

6. The dummy bearing of claim 5, wherein the material of said second split ring is non-corrosive and harder than the material of said annular member.

7. The dummy bearing of claim 6, wherein said second split ring has a plurality of cutting edges disposed thereon proximate said annular member in order to abrade the surface of said annular member in proportion to the rate of wear of said bearing.

8. The dummy bearing of claim 7, wherein said annular member is a first split ring disposed relative to said second split ring so as to form an initial clearance therebetween which is equal to the initial clearance of said bearing,
   whereby when said first split ring is abraded by said second split ring, the actual clearance is measured by inspecting and measuring the actual width of said first split ring.

9. The dummy bearing of claim 8, wherein:
   the major axis of said first split ring is perpendicular to the longitudinal axis of said shaft,
   said second split ring is coaxial with said shaft so as to form, in combination with said first split ring, a dummy radial bearing, and wherein,
   said bearing is a radial bearing.

10. The dummy bearing of claim 8, wherein:
    said cutting edges lie in a plane perpendicular to the longitudinal axis of said shaft as as to form, in combination with said first split ring, a dummy thrust bearing, and wherein,
    said bearing is a thrust bearing.

* * * * *